United States Patent [19]

Witherup et al.

[11] Patent Number: 5,288,725
[45] Date of Patent: Feb. 22, 1994

[54] PYRROLOQUINOLINE BRADYKININ ANTAGONIST

[75] Inventors: Keith M. Witherup, Lansdale; Richard W. Ransom, New Britain; Sandor L. Varga, Harleysville; Steven M. Pitzenberger, Lansdale; Victor J. Lotti, Harleysville; William J. Lumma, Pennsburg, all of Pa.

[73] Assignee: Merck & Co., Inc., Rahway, N.J.

[21] Appl. No.: 961,589

[22] Filed: Oct. 15, 1992

[51] Int. Cl.$^5$ .................. C07D 471/04; A61K 31/44
[52] U.S. Cl. ......................................... 514/292; 546/84
[58] Field of Search ........................... 546/84; 514/292

[56] References Cited

U.S. PATENT DOCUMENTS 2,691,023 10/1954 Horlein et al. ..................... 546/84

OTHER PUBLICATIONS

Khan et al., *Heterocycles* vol. 12(6) pp. 857-870 (1979).

Primary Examiner—Alan L. Rotman
Assistant Examiner—Phyllis G. Spivack
Attorney, Agent, or Firm—Catherine A. Dolan; Melvin Winokur; Paul D. Matukaitis

[57] ABSTRACT

A pyrroloquinoline compound of the following formula is disclosed:

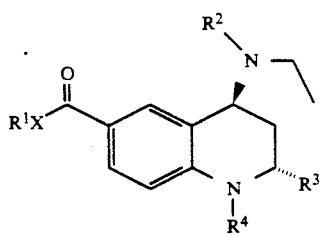

wherein
H,
$C_{1-6}$ alkyl,
$R^1$ is:

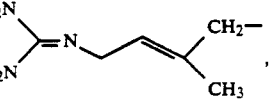

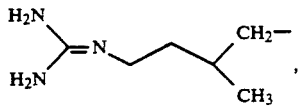

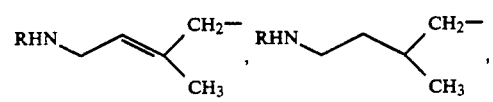

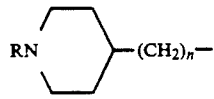

wherein R is H, $C_{1-10}$ alkyl, or $C_{1-6}$ alkyloxycarbonyl;
$R^2$ is:
H,
$C_{1-6}$ alkyl,

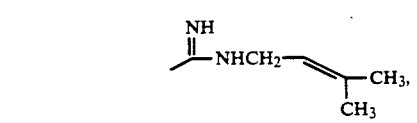

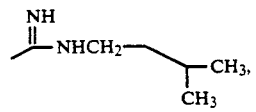

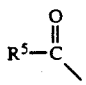

wherein $R^5$ is $C_{1-10}$ alkyl, aryl, or aryl $C_{1-10}$ alkyl;
$R^3$ is:

(Abstract continued on next page.)

(CH$_2$)$_n$NHR wherein R is H, C$_{1-6}$ alkyl, or C$_{1-6}$ alkyloxycarbonyl;

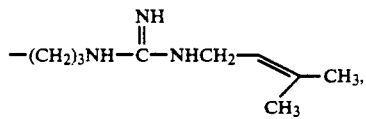

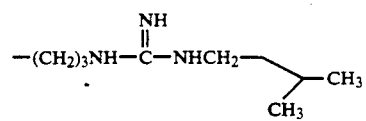

R$^4$ is:
H,

C$_{1-6}$ alkyl,
C$_{1-6}$ alkyloxycarbonyl,
RCH$_2$—, wherein R is H, C$_{1-6}$ alkyl or aryl, or

X is
O, or NR$^6$ wherein R$^6$ is equal to H or C$_{1-6}$ alkyl and n is an integer from 1–3.

The compounds of the invention exhibit bradykinin antagonist activity as well as activity with α-adrenergic, histaminergic, and muscarinic receptors.

17 Claims, No Drawings

PYRROLOQUINOLINE BRADYKININ ANTAGONIST

BACKGROUND OF THE INVENTION

The present invention is directed to novel pyrroloquinoline alkaloids which demonstrate activity against bradykinin, α-adrenergic, histaminergic, and muscarinic receptors. Known bradykinin (BK) antagonists are peptides. The present invention describes an non-peptide that is a bradykinin antagonist. BK is a hormonal nonapeptide which mediates pain, vascular permeability, inflammation, gastrointestinal function, and smooth muscle tone in vascular and other tissues. BK is one of the key mediators of the body's response to trauma and injury. BK levels are generally low until a traumatic event triggers a cascade of biochemical reactions and a rise in the concentration of BK by proteolytic generation. High molecular weight precursors, the kininogens, are found in blood and tissue. This cascade is initiated by the activation of the Hageman factor which also initiates fibrinolysis and coagulation.

Receptors for BK exist in the nervous system, epithelia, smooth muscle and fibroblasts. In each tissue type BK triggers specific responses including neurotransmitter release, muscle contraction, fluid secretion by epithelia, and the stimulation of cell growth. The initial interaction for the biological response occurs at a BK receptor site on a cell. Specific peptide BK antagonists have been developed (Vavrek, Peptides, 6, 161–165 (1985)). Their potential use includes use as anti-nociceptive and anti-inflammatory agents. BK can activate neurons and produce neurotransmitter release. It activates phospholipases C and $A_2$ resulting in the production of a number of bioactive intermediates including inositol triphosphate (Ins-1,4,5-$P_3$), diacylglycerol(-DAG) and arachidonic acid (AA) and its cyclooxygenase and lipooxygenase products. These substances cause cellular levels of cAMP, cGMP, and $Ca^{2+}$ to increase. In neurons, the most important points of action for the substances released by BK stimulation may be ion channels, Miller, R. J., Trends Neurosci., 10, 266–228 (1987).

BK released during tissue damage causes vasodilation, increased vascular permeability, altered gut motility and pain. Specific BK receptors exist in intestinal mucosa and muscle. BK and its analogs stimulate $Cl^-$ secretion by the gut epithelia. BK has a contractile effect in muscle. Manning et al., Nature, 299, 256–259 (1982).

BK can open calcium channels as indicated by the inhibitory effects of $Ca^{2+}$ channel blockers. Calcium may be involved in regulating BK receptor binding. See Innis et al., Proc. Natn. Acad. Sci., 2630–2634 (1981). BK also stimulates sodium intake and DNA synthesis. Owen et al., Cell, 32, 979–985 (1983).

Excessive kinin activity may play some role in carcinoid syndrome and in inflammatory bowel disease. Patients with ulcerative colitis have abnormally high levels of active kallikrein, the kinin-releasing enzyme, and plasma and tissue levels of peptidyl dipeptidase which degrades kinins are depressed in patients with regional enteritis. Manning et al., Nature, 299, 256–259 (1982).

The localization of BK receptors to nociceptive neurons supports a role for BK in pain mediation. Several BK antagonists block BK induced acute vascular pain in the rat. BK antagonists also relieve BK and unrate induced hyperalgesia in the rat paw. These results indicate that BK is a physiologic mediator of pain and that BK antagonists have analgesic activity in both acute and chronic pain models. The BK receptor involved in vascular pain may be different from the receptor involved in cutaneous hyperalgesia. Steranka et al., Proc. Natl. Acad. Sci. USA., 85, 3245–3249 (1988).

BK receptors have been classified as two major subtypes-$\beta_1$ and $\beta_2$. The BK metabolite des-$Arg^9$-bradykinin is a $\beta_1$ receptor agonist which has higher potency than BK but it is relatively inactive at $\beta_2$ receptors. Steranka et al., Proc. Natl. Acad. Sci. USA., 85, 3245–3249 (1988). BK receptors are G protein-coupled receptors that activate phospholipase C or phospholipase $A_2$ and increases the synthesis of inositol triphosphate or arachidonic acid. Olsen et al., J. Bio. Chem. 263, 18030–18035 (1988). G-proteins are a family of membrane proteins that become activated only after binding guanosine triphosphate (GTP). Activated G-proteins in turn activate an amplifier enzyme on the inner face of a membrane; the enzyme then converts precursor molecules into second messengers. For example, an external signal molecule (bradykinin) may bind to its cell-surface receptor (BK-2) and induce a conformational change in the receptor. This change is transmitted through the cell membrane to a G-protein, making it able to bind to GTP. Binding of GTP causes another conformational change in the G-protein that enables it to activate phospholipases $A_2$ and C. BK antagonists may be useful, therefore, to prevent the activation of G-proteins by bradykinin.

It is known that there is a large degree of heterogenicity within the muscarinic, adrenergic, and serotonergic classes of receptors. But, it is also known that "[s]imple classification of subtypes of BK receptors cannot fully account for the properties of these receptors on cells from a variety of tissues." Mahan et al., Mol. Pharmacol., 37, 785–789 (1990).

BK induces InsP formation through the activation of phosphatidylinositol-specific phospholipase C and subsequent mobilization of intracellular $Ca^{2+}$ and activation of phospholipase $A_2$, which causes the release of arachidonate and subsequent synthesis of prostaglandin $E_2$ have been found to exist in Swiss albino mouse 3T3 cells and BALBc (SV-T2) mouse 3T3 cells and involve receptors coupled to pertussis toxin-insensitive G proteins. These receptors belong to the $B_2$ subtype. Mahan et al., Mol. Pharmacol., 37, 785–789 (1990).

The effect of bradykinin on the neuroeffector junction of the isolated rat vas deferens has been studied. Llona et al., J. Pharmacol. Exp. Ther., 241, 608–614 (1987). BK potentiated the magnitude of the muscular response to the electrically driven twitches and contracted the smooth muscle generating an increased muscle tone. The former action is referred to as the neurogenic or presynaptic effect and the latter is called the musculotropic or postjunctional action. The rat vas deferens contains bradykinin receptors on the nerve endings and on smooth muscle membrane. The structural prerequisites for the activation of these receptor sites appear to be slightly different.

These results support the existence of $B_2$ receptor subtypes. Des-$Arg^9$-BK and des-$Arg^9$-[$Leu^8$]-BK are inactive in causing either pre- or postsynaptic BK like responses and incubation of des-$Arg^9$-[$Leu^8$]-BK at high concentrations failed to antagonize BK responses in the vas deferens. This peptide is a known $B_1$ antagonist. The authors suggest that there are several classes of BK-2 receptors. Llona et al., *J. Pharmacol. Exp. Ther.*, 241, 613 (1987). See also Brass et al., *Br. J. Pharmacol.*, 94, 3–5 (1988).

As indicated, BK mediates vasodilation, pain and smooth muscle contraction in a number of tissues. Many of these biological actions may result from the release of arachidonic acid and its metabolites. The major metabolite in Swiss 3T3 cells (fibroblasts) is $PGE_2$ which induces smooth muscle contraction, mitogenesis, an increase in intracellular free calcium and stimulates adenylate cyclase(to produce cAMP). BK activates phospholipases which control intracellular arachidonate. Conklin et al., *J. Pharmacol. Exp. Ther.*, 244, 646–649 (1988).

Phospholipases are considered to be the rate limiting enzymes in receptor mediated arachidonate release. BK activates $PLA_2$, a phospholipase which cleaves arachidonic acid directly from the parent phospholipid. In contrast, BK in BPAE cells (bovine pulmonary artery endothelial cells) stimulates activity of a phosphatidylcholine-specific PLC which provides arachidonate substrate for $PGI_2$ synthesis. The authors conclude that the BK receptors are pharmacologically distinct and that more BK subtypes exist beyond $BK_1$ and $BK_2$. Conklin et al., *J. Pharmacol. Exp. Ther.*, 244, 646–649 (1988). To further clarify the role of bradykinin and express the need for an effective bradykinin antagonist, kinins are released in response to tissue injury and activate sensory pain fibers, contract venous smooth muscle and stimulate prostacyclin ($PGI_2$) and endothelium derived relaxing factor (EDRF) synthesis. Blood flow to the damaged area and vascular permeability increase to cause inflammation. Plevin et al., *Trends Pharmacol. Sci.*, 9, 387–389 (1988). Multiple $\beta_2$ BK receptors in mammalian tissues are present. The tissues include guinea-pig ileum, vas deferens prejunctional, N1E-115 cells (neuronal cell line), rat uterus, and guinea-pig trachea (endothelial cells-BK linked to second messenger and coupled to a G-protein). There is a need, therefore, for a bradykinin antagonist which is useful in the treatment of a number of disorders in which bradykinin plays a role. Pharmacological agents containing guanidine moieties are known. See U.S. Pat. Nos. 5,059,624 and 5,028,613 describes tricyclic pyrroloquinoline alkaloids isolated and purfied from certain marine sponges which exhibit antitumor and antimicrobial activity. The instant invention, however, claims a novel pyrroloquinoline guanidine compound that is highly active as a bradykinin antagonist and is therefore useful to treat bradykinin associated disorders.

SUMMARY OF THE INVENTION

The present invention is a novel bradykinin antagonist of the formula:

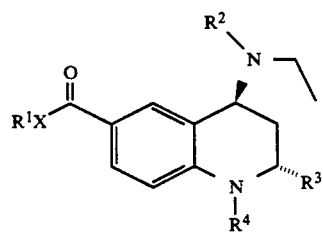

wherein
$R^1$ is:
H,
$C_{1-6}$ alkyl,

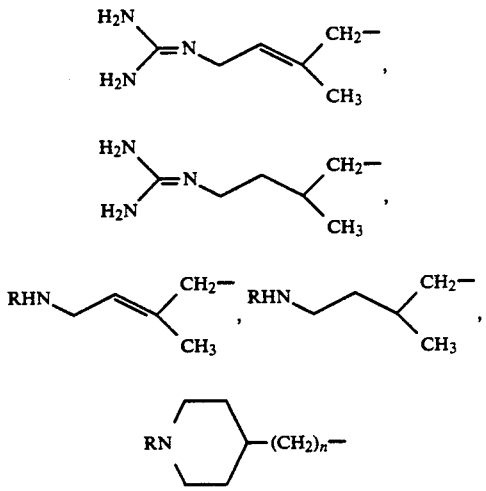

wherein R is H, $C_{1-10}$ alkyl, or $C_{1-6}$ alkyloxycarbonyl;

$R^2$ is:
H,
$C_{1-6}$ alkyl,

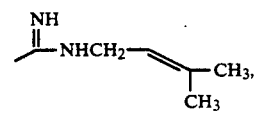

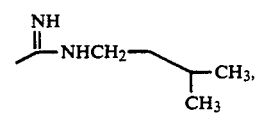

wherein $R^5$ is $C_{1-10}$ alkyl, aryl, or aryl $C_{1-10}$ alkyl;

$R^3$ is:
$(CH_2)_nNHR$ wherein R is H, $C_{1-6}$ alkyl, or $C_{1-6}$ alkyloxycarbonyl and $(CH_2)_n$ is straight chain alkyl;

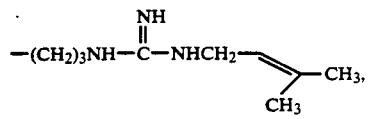

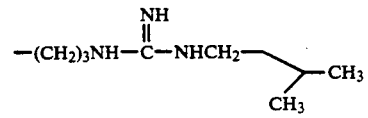

$R^4$ is:
H,
$C_{1-6}$ alkyl,
$C_{1-6}$ alkyloxycarbonyl,
$RCH_2$-, wherein R is H, $C_{1-6}$ alkyl or aryl, or

X is
O, or NR$^6$ wherein R$^6$ is equal to H or C$_{1-6}$ alkyl and n is an integer from 1-3.

The instant invention claims compounds and the pharmaceutically acceptable salts of the formula:

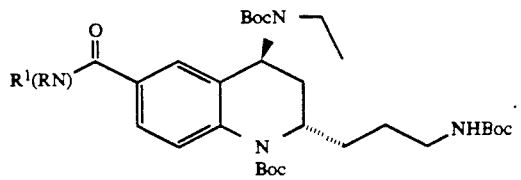

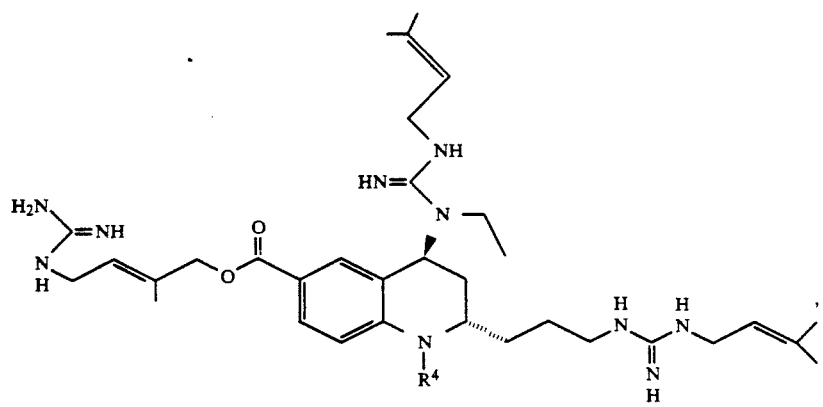

or

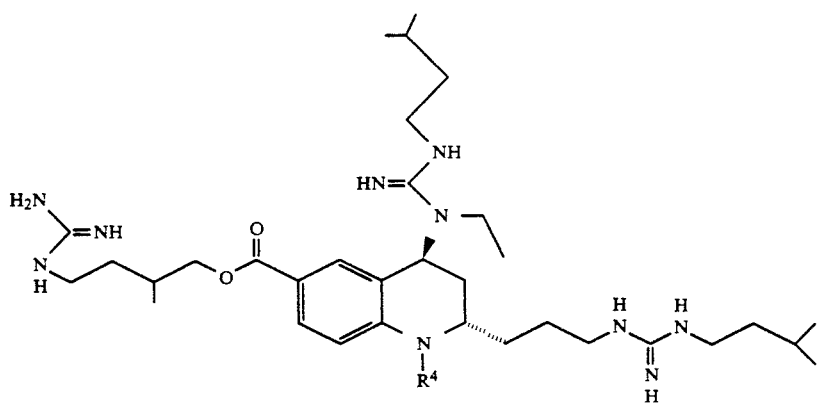

wherein R$^4$ is H or CH$_3$.

Compounds of the following formula are also claimed in the instant invention:

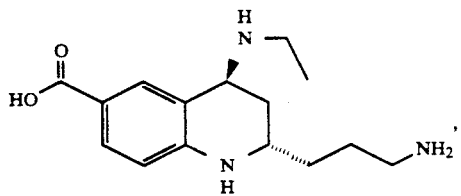

or

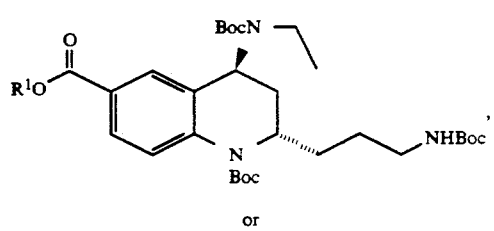

or

The latter two compounds shown above are useful as intermediates in the production of the receptor antagonists described and claimed in the instant specification. The invention also encompasses a method of inhibiting a bradykinin receptor in a mammal in need thereof comprising administering a pharmaceutically effective amount of the compounds claimed in the instant invention. But, compounds of the formula:

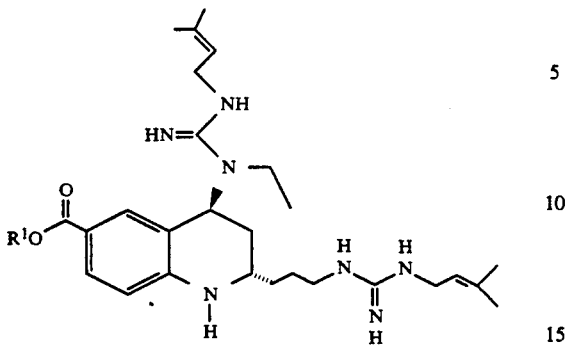

wherein $R^1$ is H or $CH_3$ are not utilized as bradykinin B1 BK or B2 BK receptor antagonists but may be useful as either chemical intermediates in the production of compounds which are bradykinin antagonists or are useful as antagonists of the other receptor sites as described herein. A method of treating pain and inflammation in a mammal in need thereof comprising administering a pharmaceutically effective amount of the claimed compounds is also claimed. A method of treating allergy symptoms in a mammal in need thereof comprising administering a pharmaceutically effective amount of the claimed compounds is also within the scope of the instant invention. Furthermore, the invention encompasses a method of inhibiting growth of human (stromal) breast tumors. A pharmaceutical composition comprising the claimed compounds and a pharmaceutically acceptable carrier is also claimed. A method of inhibiting an $\alpha_1$-adrenergic receptor in a mammal in need of treatment thereof comprising administering a pharmaceutically effective amount of the pharmaceutical composition; a method of inhibiting a muscarinic receptor in a mammal in need of treatment thereof comprising administering a pharmaceutically effective amount of the pharmaceutical composition; and a method of inhibiting an $H_1$-histamine receptor in a mammal in need of treatment thereof comprising administering a pharmaceutically effective amount of the pharmaceutical composition is claimed.

DETAILED DESCRIPTION OF THE INVENTION

The present invention is a compound of the formula:

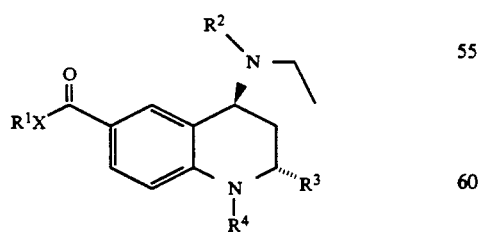

and the pharmaceutically acceptable salts thereof wherein
$R^1$ is:
H,
$C_{1-6}$ alkyl,

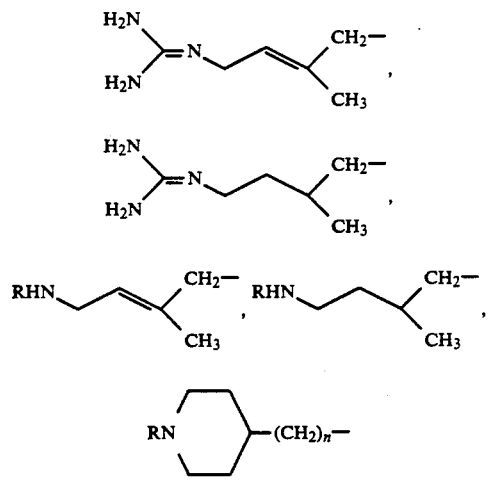

wherein R is H, $C_{1-10}$ alkyl, or $C_{1-6}$ alkyloxycarbonyl;
$R^2$ is:
H,
$C_{1-6}$ alkyl,

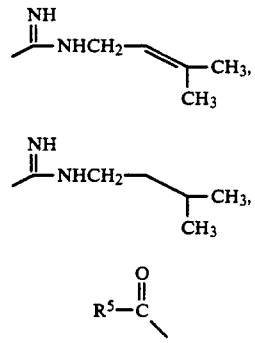

wherein $R^5$ is $C_{1-10}$ alkyl, aryl, or aryl $C_{1-10}$ alkyl;
$R^3$ is:
$(CH_2)_n NHR$ wherein R is H, $C_{1-6}$ alkyl, or $C_{1-6}$ alkyloxycarbonyl;

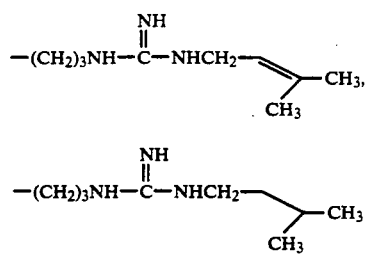

$R^4$ is:
H,
$C_{1-6}$ alkyl,
$C_{1-6}$ alkyloxycarbonyl,
$RCH_2$-, wherein R is H, $C_{1-6}$ alkyl or aryl, or

X is

O, or $NR^6$ wherein $R^6$ is equal to H or $C_{1-6}$ alkyl and n is an integer from 1-3.

The present invention relates to new guanidine alkaloids having bradykinin antagonist activity and/or activity against histaminergic, α-adrenergic, and muscarinic receptors and to compositions containing the same. The compositions are useful in the treatment of the symptoms of allergies and colds and in the treatment of pain and inflammation associated with the release and action of bradykinin. There are a number of bradykinin antagonists known but, all are peptide analogs. The compound(s) disclosed in this invention are non-peptide compounds which are readily prepared by extraction, purification, and/òr derivitization from plant materials. Advantageously, the compounds disclosed herein are obtained from readily available plant materials after purification and extraction. The disclosed process for producing the claimed compounds obviates the need for complex organic syntheses of the multi-atom compound since it may be obtained from the plant species *Martinella iquitosensis*. The compounds derived after the extensive purification and extraction procedure may readily be modified by chemical synthesis to produce compounds claimed in the instant invention. Accordingly, the object of the present invention is to provide useful quantities of the claimed compounds via economically convenient extraction and purification procedures. Compounds extracted and purified from the plant species *Martinella iquitosensis* exhibit remarkable activity against various receptors including bradykinin receptors, muscarinic receptors, α-adrenergic receptors and histaminergic receptors. The invention therefore claims a new class of bradykinin receptor antagonists as shown above. Advantageously, a compound of the formula:

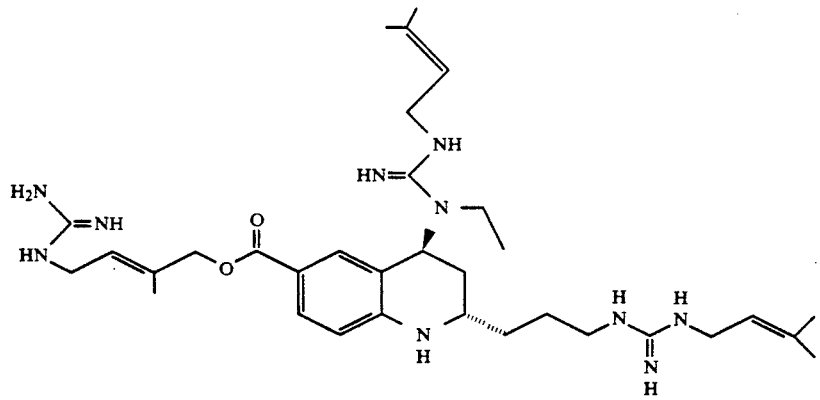

is used as a bradykinin receptor antagonist. The claimed compounds may also be formulated in suitable pharmaceutical compositions and formulations in order to effectively treat a mammal in need of treatment thereof.

The claimed invention pertains to novel compounds isolated from a certain plant species of the Bignoniaceae family. These compounds have been shown to possess bradykinin antagonist activity as well as activity against other receptors including the muscarinic, α-adrenergic, and histaminergic receptors. The subject invention pertains to the claimed compounds as well as pharmaceutical compositions containing them. The pharmaceutical compositions containing the active ingredients claimed in the instant invention may be useful for a multitude of bradykinin related disorders including the symptoms of allergies and colds and pain and inflammation. The claimed invention also relates to methods of administering the claimed compounds to treat bradykinin related disorders or the symptomatic effects of bradykinin related disorders. Of course, various derivatives of the isolated compounds may be produced by well known synthetic procedures. The parent compounds may be isolated from the plant species as described below.

A complete taxonomic description of the species is as follows: Division Magnoliophyta, Class Magnoliopsida, Subclass Asteridae, Order Scrophulariales, Family Bignoneaceae, Genus Martinella, Species iquitosensis. The family contains about 120 genera and 650 species, mostly of tropical and subtropical distribution but with a few temperate zone species such as *Campsis radicans, Bignonia capreolata* and *Catalpa*. The economical importance of the Bignoniaceae is for its woody ornamental vines and trees. Chemical characterization of the preferred compounds of the present invention will be described in the Examples section. The compounds of the present invention may readily be prepared by following the described extraction, purification, and/or synthetic procedures. Initially, the root of the plant species *Martinella iquitosensis* of the Bignoniaceae family is collected in Peru. A voucher is on deposit at the Missouri Botanical Garden. The root is air dried, milled and extracted with methylene chloride/methanol (1:1) to yield the desired grams of an organic soluble oil depending upon the number of grams of root material. The oil obtained is roughly 10% by weight of the mass of root initially extracted. The organic extract is then passed through a 31 gram plug of $C_{18}$ adsorbent (Vydac, 15-30 um), eluted with $H_2O$ followed by 100% methanol. The methanolic fraction is then subjected repeatedly to prep. HPLC (Vydac $C_{18}$, 10 um, 22.5 mm×250 mm, gradient elution MeCN (1% TFA)/$H_2O$ (1% TFA) 0:100 to 60:40 in 1 hour., UV 330 nm) to yield the preferred compound. This compound is further derivatized according to the schemes below to prepare the compounds claimed in the instant invention.

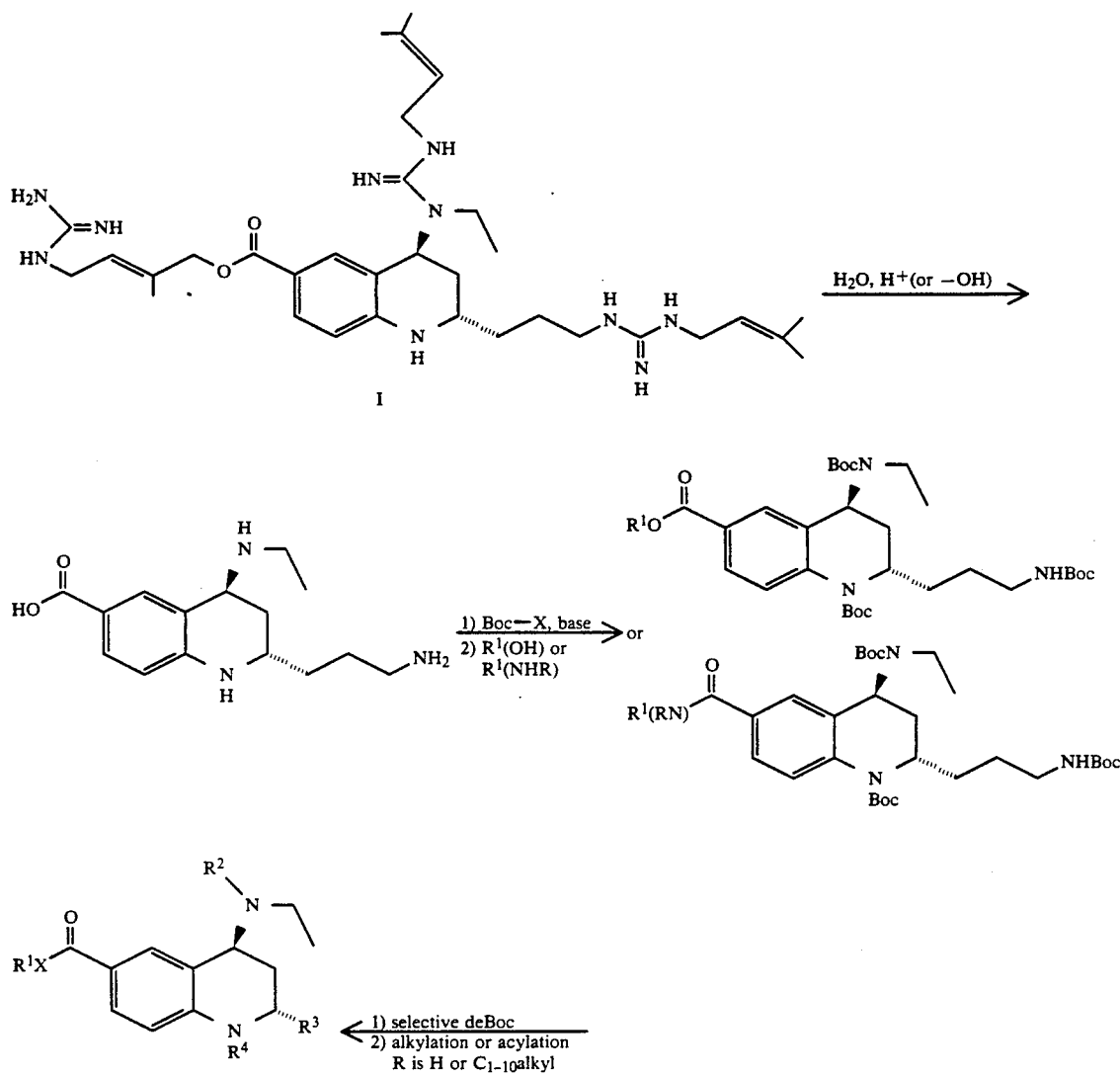
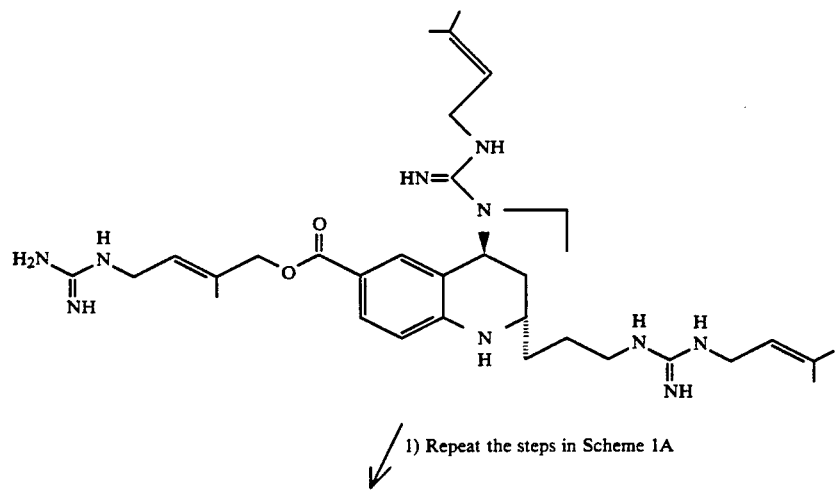
Scheme 1A

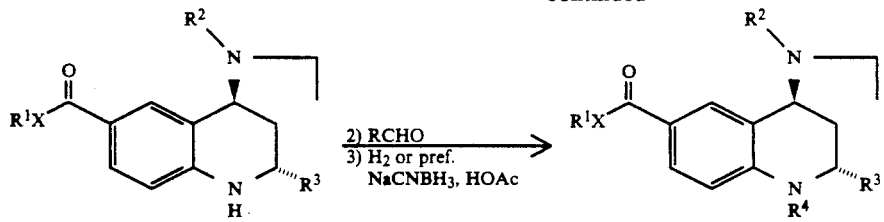

R₄ = RCH₂— and R = H, lower alkyl, Ar
Ar = Ph, pMeOPh

In steps 2 and 3, the other free amines must be protected in order to selectively react at the R⁴ N, likewise the same reaction may be run at the R² position or on the free amine at the R³ amine if the other free amines are protected.

Scheme 1B

Acid hydrolysis of compound I followed by protection of the free amino groups with t-butoxycarbonyl or other suitable protecting group and subsequent reaction with R¹OH or amidation with a substituted amine such as R¹(NHR) yields either the ester or substituted amide derivative shown in the above scheme (1A and 1B). Subsequent deprotection and alkylation or acylation produces a member of the generic class as shown above and as claimed in the instant invention. It is understood that any suitable protecting group for a carboxylic acid or for an amine may be used to create compounds within the scope of the present invention. For example, standard protecting groups for carboxylic acids include esters, such as methyl esters or substituted methyl esters or ethyl esters or substituted ethyl esters. Substituted benzyl esters, silyl esters, activated esters and miscellaneous derivatives as described in *Protecting Groups in Organic Synthesis*, T. Green and P. Wuts, John Wiley and Sons (1991) may be used and are within the scope of the present invention. The amino groups may be protected with a number of different reagents to form carbamates, amides, N-alkyl or aryl amines, imines, enamines, and N-sulfonyl or sulfenyl derivatives. The Boc group is preferably used to protect amines within the scope of the present invention.

Compounds of the invention may also be prepared according to the following:

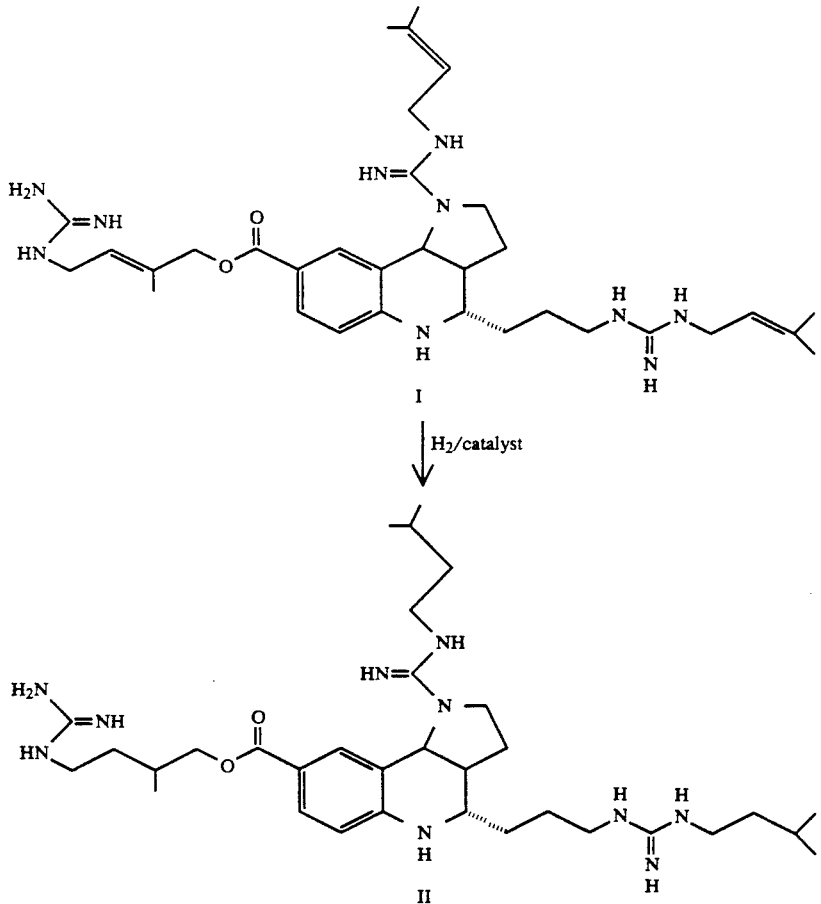

Scheme 2

Reduction of compound I using hydrogen and a metal catalyst produces the reduced guanidine derivative II shown above.

Alternative routes to produce or obtain compounds within the pyrrolidine class other than through extraction or purification of natural products include organic synthesis. For example, the basic tricyclic skeleton of the claimed compound may be prepared according to the procedure described by Martin et al. Tetrahedron Letters, 30 (50), 7017-7020 (1989):

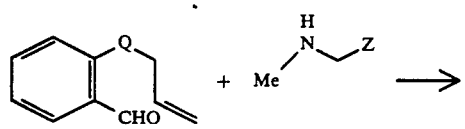

Q is NSO$_2$Me;
Z is P(O)(O-i-Pr)$_2$, or CN.

in Scheme 3 could produce a compound of the formula:

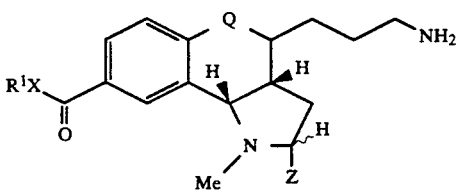

which could be further derivatized to I or II.

The basic pyrroloquinoline ring system has also been prepared by other chemical means. For example, Khan et al. in Heterocyles 12 (6) 857 (1979) describes the synthesis of various substituted pyrroloquinolines:

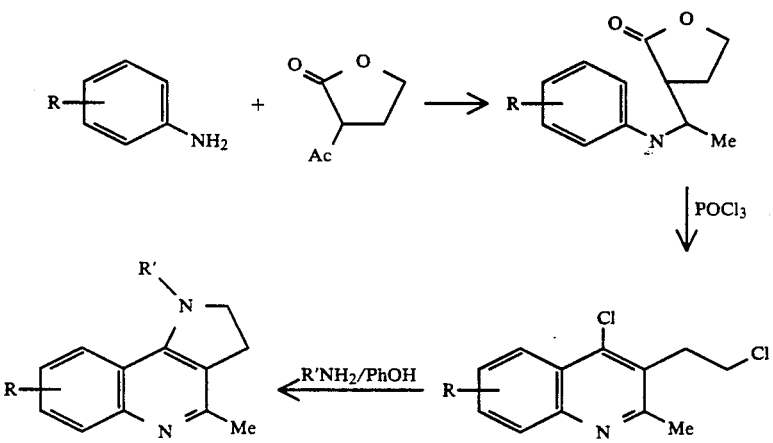

Scheme 4

This reference disclosed that some pyrroloquinolines have activity as hypotensive agents, as antimalarials or as amebicides.

The term "pharmaceutically acceptable salts" shall mean non-toxic salts of the compounds of this invention which are generally prepared by reacting the free base with a suitable organic or inorganic acid. Representative salts include the following salts: Acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, glucoheptanate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, pantothenate, phosphate/diphosphate, polygalactouronate, salicylate, stearate, subacetate, succinate, tannate, tartrate, teoclate, tosylate, triethiodide, valerate.

The term "pharmaceutically effective amount" shall mean that amount of a drug or pharmaceutical agent that will elicit the biological or medical response of a tissue, system or animal that is being sought by a researcher or clinician.

The term "aryl" shall mean a mono- or polycyclic system composed of 5- and/or 6-membered aromatic rings containing 0, 1, 2, 3, or 4 heteroatoms chosen from N, O or S and either unsubstituted or substituted with

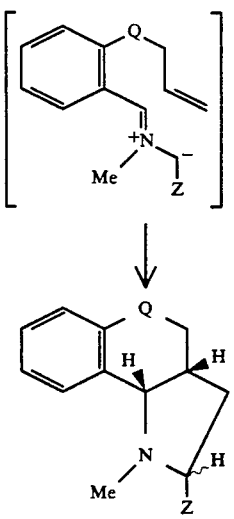

Scheme 3

Functionalizing the starting aromatic system with an ester moiety or an amide meta to the aldehyde group and with a C$_{1-3}$ alkylamine at the carbon adjacent to Q typical aromatic substituents including but not limited to halogens, hydroxy, and methoxy.

The term "alkyl" shall mean straight or branched alkane, alkene or alkyne. The term "alkoxy" shall be taken to include an alkyl portion where alkyl is as defined above.

The terms "arylalkyl" and "alkylaryl" shall be taken to include an alkyl portion where alkyl is as defined above and to include an aryl portion where aryl is as defined above. The $C_{0-n}$ or $C_{1-n}$ designation where n may be an integer from 1-10 or 2-10 respectively refers to the alkyl component of the arylalkyl or alkylaryl unit.

The term "halogen" shall include fluorine, chlorine, iodine and bromine. The term "oxy" shall mean an oxygen (O) atom. The term "oxo" refers to a bivalent oxygen atom (=O). The term "thio" shall mean a sulfur (S) atom.

BOC(Boc) is defined as t-butyloxybcarbonyl and is typically used to protect the amino group.

Following are examples which illustrate procedures, including the best mode, for practicing the invention. These examples should not be considered to be limiting.

EXAMPLES

High resolution FABMS (pos.): obs. m/z 620. 43483, calc. 620.4358 for $C_{33}H_{55}N_{10}O_2$.

FABMS (pos.) m/z 621 $(M+H)^+$, 496 $(MH^+ -108)^+$, m/z 108=free alcohol of ester side chain. No other diagnostic peaks present.

UV $\lambda_{max}$ ($H_2O$, pH 7.45) 314 nm ($\epsilon$12,457 cm$^{-1}$M$^{-1}$) NMR—$^1$H at 499.843 MHz; $^{13}$C at 125.697 MHz; F at 282.2 MHz. The structure of I was determined from its proton and carbon NMR spectra (see Table 1). Carbon NMR spectroscopy revealed that the 052-2 sample to be a trifluoroacetic acid salt with 33 carbons for the conjugate base and 2 carbons (quartets at 158.3 and 117.1 ppm) for trifluoroacetic acid (TFA). Quantitative fluorine NMR showed that 2.8 equivalents of TFA were present, suggesting the presence of 3 basic sites in the parent molecule. The carbons of I can be grouped into the following types: 10 quaternary (all in the aromatic/carbonyl regions), 3 aromatic CH, 3 $CH_2$, 6 $CH_2X$, 3 CHX, 3 olefinic CH, and 5 $CH_3$. From the results of carbon-proton correlation data, there are 42 carbon-bound protons. Integration of the 1D proton spectrum suggests at least 10 exchangeable proton resonances are present in the salt.

Compound I is depicted numerically as shown on the following page:

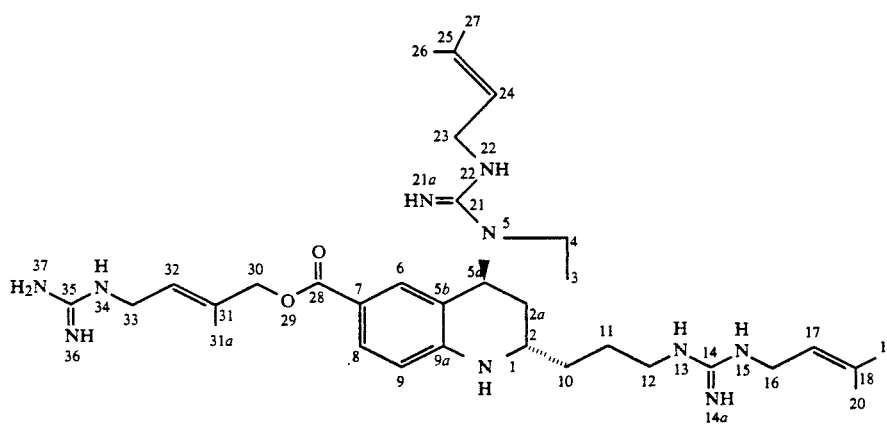

EXAMPLE 1

Isolation of Novel Compounds 17.1 grams of a root taken from the plant species *Martinella iquitosensis* of the Bignoniaceae was collected in Peru with a voucher on deposit at the Missouri Botanical Garden. The root was air dried, milled and extracted with methylene chloride/methanol (1:1) to yield 1.6 grams of an organic soluble oil. 0.733 grams of this organic extract was passed through a 31 gram plug of $C_{18}$ adsorbent (Vydac, 15-30 um), eluted with 200 ml $H_2O$ followed by 200 ml 100% methanol. The methanolic fraction (0.202 g) was then subjected repeatedly to prep. HPLC (Vydac $C_{18}$, 10 um, 22.5 mm×250 mm, gradient elution MeCN (1% TFA)/$H_2O$ (1% TFA) 0:100 to 60:40 in 1 hour., UV 330 nm) to yield approximately 47 mg of I.

EXAMPLE 2

Physical and Spectral Data of I

Physical and Spectral Data for I.
IR (KBr) 3315, 3160, 1665, 1600, 1190 cm$^{-1}$.
$[\alpha]^{25°}D = +9.412°$.

Table 1. Carbon and Proton Chemical Shifts for (I) in $d_6$-DMSO.

TABLE 1

| Carbon and Proton Chemical Shifts for (I) in $d_6$-DMSO. | | |
|---|---|---|
| Position | Carbon Shift (ppm)$^a$ | Proton Shift (ppm)$^a$ |
| 1 | — | 7.20 |
| 2 | 49.0 | 3.30 |
| 2$^a$ | 39.2 | 2.44 |
| 3 | 26.2 | 2.07, 1.68 |
| 4 | 45.7 | 3.38 |
| 5$^a$ | 52.9 | 5.32 |
| 5$^b$ | 115.9 | — |
| 6 | 130.4 | 7.66 |
| 7 | 115.6 | — |
| 8 | 129.7 | 7.58 |
| 9 | 113.3 | 6.61 |
| 9$^a$ | 146.7 | — |
| 10 | 33.3 | 1.44 |
| 11 | 25.2 | 1.61 |
| 12 | 40.6 | 3.13 |
| 13 | — | 7.65 |
| 14 | 155.4 | — |
| 14$^a$ | — | 7.44 |
| 15 | — | 7.61 |
| 16 | 38.9 | 3.73 |
| 17 | 119.1 | 5.17 |
| 18 | 135.8 | — |
| 19 | 25.2 | 1.70 |

TABLE 1-continued

Carbon and Proton Chemical Shifts for (I) in d₆-DMSO.

| Position | Carbon Shift (ppm)[a] | Proton Shift (ppm)[a] |
|---|---|---|
| 20 | 17.7 | 1.64 |
| 21 | 154.3 | — |
| 21[a] | — | 7.73 |
| 22 | — | 7.76 |
| 23 | 39.9 | 3.86, 3.93 |
| 24 | 119.4 | 5.30 |
| 25 | 135.5 | — |
| 26 | 17.8 | 1.69 |
| 27 | 25.3 | 1.74 |
| 28 | 165.1 | — |
| 30 | 67.6 | 4.59, 4.64 |
| 31 | 134.7 | — |
| 31[a] | 13.7 | 1.71 |
| 32 | 121.6 | 5.51 |
| 33 | 38.3 | 3.81 |
| 34 | — | 7.83 |
| 35 | 156.7 | — |
| 36, 37 | — | 7.26 (very broad) |

[a]Carbon and proton shifts are for separate batches of I
[b]Chemical shifts of the exchangable NHs are dependent on pD, concentration and water content of the sample The combined results of 1) the proton 1D spectrum, 2) a proton-proton correlation experiment (COSY), and 3) a proton-detected carbon-proton correlation experiment (HMQC) showed six cascades of protons. The first and most obvious grouping of protons belong to a 1,2,4-trisubstituted aromatic ring. The upfield shift (6.61 ppm) of the proton ortho to the 1-substituent in this pattern is characteristic of either oxygen or nitrogen substitution in the 1 position. The relative downfield shifts of the remaining two protons show that a carbonyl or carbonyl like function resides at the 4-position of the aromatic ring.

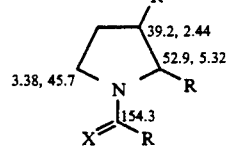

Two proton spin systems are found on 4 carbon fragments which have heteroatom substituents attached to the end carbons. From the chemical shifts of the end carbons, it is likely that the heteroatoms are nitrogens. The spin systems differ in that one is clearly part of an aliphatic chain with 3 sequential CH₂ units and a terminal methine (see B below). The other spin system is part of a 5-membered ring where the end heteroatoms are actually a common nitrogen atom (see C below). The ring structure was suggested by an NOE which was observed between the methine and the methylene and the opposite end of the fragment. The ring structure was further corroborated by a long-range carbon-proton correlation (HMBC experiment) from the terminal methine proton to the methylene carbon at the other end.

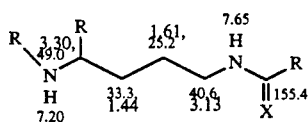

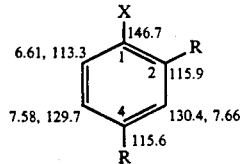

The next two spin systems were found to belong to isoprenyl derivatives which differed only slightly in their chemical shifts. Carbon chemical shifts and proton couplings indicated that the attachment to each isoprenyl group is via an NH. The methyl groups of each isoprenyl group were uniquely identified by NOE enhancements with neighboring protons.

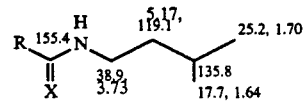

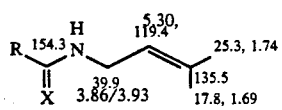

The final proton spin system is a an isoprenyl derivative. As shown in F below, one of the methyl groups was found to be substituted with a heteroatom. The chemical shift of the carbon is indicative of oxygen substitution. The olefin was determined to be in the E configuration from NOE data.

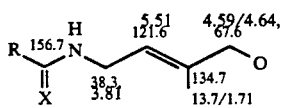

The above fragments were assembled with the aid of proton-detected long-range carbon-proton correlation (HMBC) and 2D NOE (NOESY) experiments. The 5.32-ppm proton of fragment C and the 3.86/3.93 ppm methylene protons of fragment E correlate to the same downfield carbon (154.3 ppm) establishing a connection between C, E, and this carbon. This 154.3-ppm carbon is part of a guanidinium group by the virtue of its chemical shift and attached exchangeable protons. Similarly, the 3.13 ppm proton of fragment B and the 3.73 ppm proton of fragment D correlate to the same guanidium carbon (155.4 ppm). A strong NOE was observed between the 6.61-ppm aromatic proton of fragment A and the 7.20-ppm NH of fragment B suggesting that fragment B is attached to the aromatic ring via this NH. The upfield position (6.61 ppm) of the proton ortho to the point of attachment is consistent with the suggested bond between fragments A and B. A bond between the 5.32-ppm methine of fragment C and the aromatic ring (fragment A) was deduced from correlations between the methine proton and 3 aromatic carbons. Another attachment to fragment C was observed in a long range correlation between the 3.30-ppm methine proton of fragment B and the 52.9-ppm carbon of fragment C. This later correlation fits well with fragments A, B, and C being fused to make a piperidine ring as in structure I. The final attachment between fragments A and F was observed by correlations of the 4.59/4.64-ppm methylene protons of fragment F and the 7.58 and 7.66 ppm protons of fragment A to a common carbon at 165.1 ppm. The chemical shifts of the protons and carbons surrounding this point of attachment are indicative of an ester moiety.

The stereochemistry of the ring juncture in I was found to be cis. A large, trans-diaxial coupling would have been expected between the bridgehead protons if the ring juncture were trans. The observed coupling is 5 Hz which agrees well with expectation based on models of possible cis conformers. The sterochemistry of the adjacent substituent in the 2-position was found to be trans relative to the ring juncture. A strong NOE was observed between the H-5a bridgehead proton and H-10 of the sidechain. This NOE is only possible if H-5a and the sidechain reside on the same face of the piperidine ring and they both occupy pseudo-axial positions. The H-2 to H-2a coupling was found to be small (<2 Hz) based on the absence of a correlation between these protons in the COSY spectrum. This is in accord with H-2 and H-2a occupying pseudo-equatorial positions on the piperidine ring.

EXAMPLE 3

Antagonist Properties of Compound I

Radioligand binding assays were employed to study the interaction of I at BK $\beta_2$, $\alpha_1$-adrenergic, and muscarinic receptors. [$^3$H] BK binding to guinea pig ileum membranes were as described in Ransom et al., Biochem. Pharmacol., 43, 1823 (1992). I inhibited [$^3$H] BK binding with an IC$_{50}$=0.2 $\mu$M. [$^3$H] Prazosin was used to lable $\alpha_1$-adrenergic receptors in rat brain as described in Battaglia et. al., J. Neurochem., 41,538 (1983). The IC$_{50}$ value of I in these experiments was 0.06 $\mu$M. This result is consistent with the a1-receptor antagonist activity of the compound observed in the organ bath experiments using rabbit aorta. [$^3$H] Quinuclidinyl benzilate was used to label cholinergic muscarinic receptors in rat crebral cortex membranes, rat cardiac membranes, and guinea pig ileum membranes as described by Watson et. al., J. Pharmacol. Exp. Ther., 237,419 (1986). I blocked binding with IC$_{50}$ value of 0.1 $\mu$M in each of the preparations.

Antagonism of BK-$\beta_1$ receptors was measured using spiral strips of rabbit thoracic aorta as described by Regoli et. al., Eur. J. Pharmacol., 127,219 (1986). Concentration-response curves were obtained using the $\beta$1 agonist des Arg$^9$-BK in the absence and presence of fixed concentrations of I. Analysis of the data by the method of Schild [Br. J. Pharmacol., 14, 48 (1959)] indicated that I behaves as a competitive $\beta$1 receptor antagonist with a pA2 value of 5.7.

The $\alpha_1$-adrenergic and H$_1$ histaminergic receptor activity of compounds were also assessed using rabbit aorta with norepinephrine and histamine, respectively, as agonists. I acted as a competitive antagonist at both receptors with pA2 values of 7.1 at the $\alpha_1$ receptor and 5.9 at histamine H$_1$ receptor.

The compounds of the invention are useful for a number of therapeutic purposes. It is apparent from the biological testing of these compounds that they are potent antagonists of bradykinin receptors as well as antagonists of other biological receptors as recited herein. Preferentially, the compounds disclosed herein are used as bradykinin antagonists. Therapeutic application of the new compounds and compositions containing them can be contemplated by any suitable conventional means of administering anti-allergy or anti-inflammatory drugs. The compounds of the invention may also have use as starting materials for other useful compounds and compositions.

The present composition may be administered in the form of tablets, caplets, gelcaps, capsules, elixirs, syrups, or suspensions. For oral administration, the active ingredients may be admixed with a pharmaceutically acceptable diluent such as lactose, sucrose, cellulose, dicalcium phosphate, calcium sulfate, mannitol, and, in a liquid composition, ethyl alcohol. Acceptable emulsifying or suspending agents such as PVP, gelatin, natural sugars, corn sweeteners, natural and synthetic gums such as acacia, sodium alginate, guar gum, agar, bentonite, carboxymethylcellulose sodium, polyethylene glycol and waxes, may also be admixed with the active components. Where necessary, lubricants such as magnesium stearic acid talc or magnesium stearate, and disintegrators or superdisintegrators such as starch, sodium starch glycolate or cross-linked PVP may also be included. Electrolytes such as dicalcium phosphate, sodium benzoate, sodium acetate and sodium chloride may also be used.

The active components may also be formulated in sustained release or effervescent formulations. These formulations depending upon whether they are sustained release or effervescent may be employed in oral, dermal, rectal or vaginal administrations. The sustained release formulations also include layered formulations which provide for distinct release ratio and thus may be more effective in allowing for short and long term relief.

The dosage administration to a host in need thereof of an effective amount of the compounds claimed in the invention to relieve pain or inflammation or allergy symptoms will depend upon the identity of the pain or allergy source as well as the type of host involved, its age, weight, health, kind of concurrent treatment and other factors known to those skilled in the art. The particular formulations and compositions claimed in the instant invention and used to administer or deliver the active ingredient of the instant invention may be those typical compositions or formulations well known to those skilled in the art. In general, the compositions of the claimed invention will be formulated so that a pharmaceutically effective amount of the active ingredient is combined with a suitable carrier in order to effectively administer the active compound to the host in need thereof. Such hosts include mammals such as man and horses, pigs, dogs, cats and other organisms in need of relief of pain and inflammation or allergy symptoms.

It will be understood by those skilled in the art that the examples and embodiments described herein are non-limiting and various minor modifications are included within the scope of the instant invention.

What is claimed is:

1. A compound of the formula:

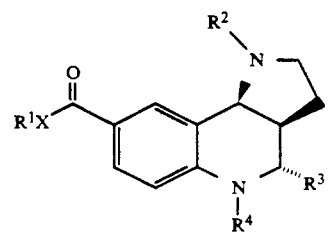

and the pharmaceutically acceptable salts thereof, wherein:

$R^1$ is
H,
$C_{1-6}$ alkyl,

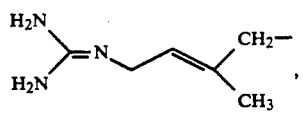

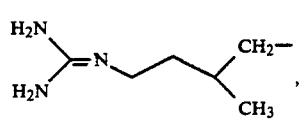

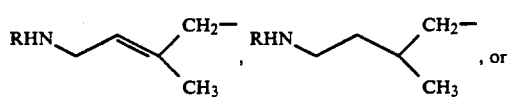, or

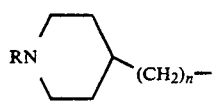

wherein R is H, $C_{1-10}$ alkyl, or $C_{1-6}$ alkyloxycarbonyl;

$R^2$ is:
H,
$C_{1-6}$ alkyl,

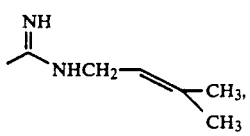

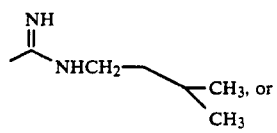, or

wherein $R^5$ is $C_{1-10}$ alkyl, aryl, or aryl $C_{1-10}$ alkyl wherein aryl is phenyl or methoxy phenyl;

$R^3$ is: $-(CH_2)_nNHR$ wherein R is H, $C_{1-6}$ alkyl, or $C_{1-6}$ alkyloxycarbonyl and $-(CH_2)_n$ is straight chain alkyl;

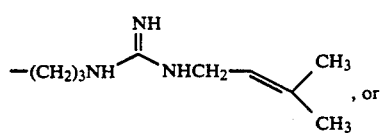, or

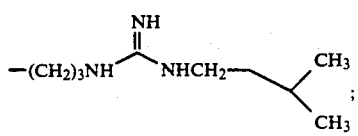

$R^4$ is:

H,
$C_{1-6}$ alkyl,
$C_{1-6}$ alkyloxycarbonyl,
$RCH_2$—, wherein R is H, $C_{1-6}$ alkyl or aryl wherein aryl is phenyl, or methoxy phenyl; or

;

X is:
O, or $NR^6$ wherein $R^6$ is equal to H or $C_{1-6}$ alkyl and n is an integer from 1–3.

2. The compound according to claim 1 and the pharmaceutically acceptable salts wherein:

$R^1$ is:

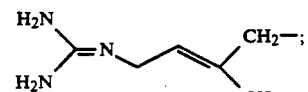

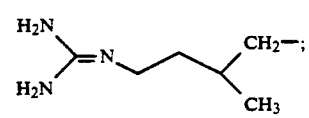

$R^2$ is:

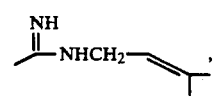

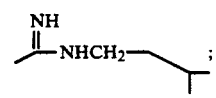

$R^3$ is:
$(CH_2)_3NHR$ wherein R is H, $C_{1-6}$ alkyl, or $C_{1-6}$ alkyloxycarbonyl;

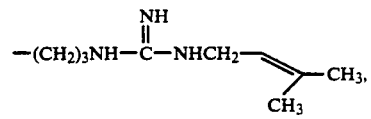

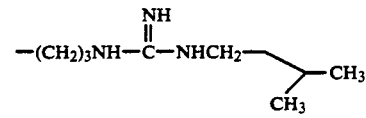

$R^4$ is:
H,
$C_{1-6}$ alkyl,
$C_{1-6}$ alkyloxycarbonyl,
$RCH_2$—, wherein R is H, $C_{1-6}$ alkyl or aryl, or

X is:
O, or $NR^6$ wherein $R^6$ is equal to H or $C_{1-6}$ alkyl.

3. The compound according to claim 2 and the pharmaceutically acceptable salts of the formula:

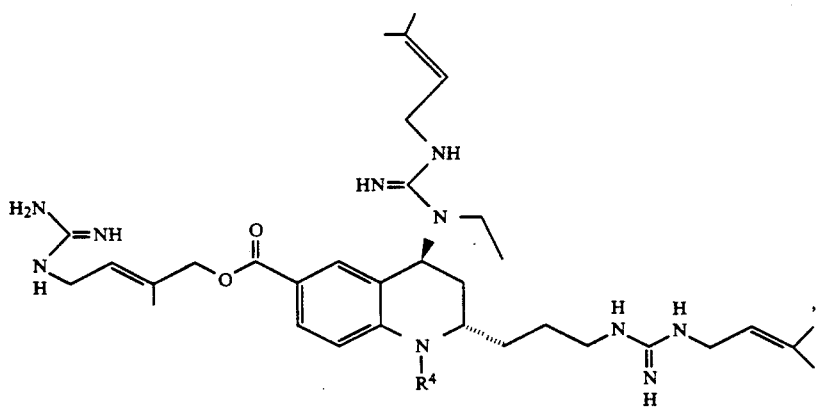

or

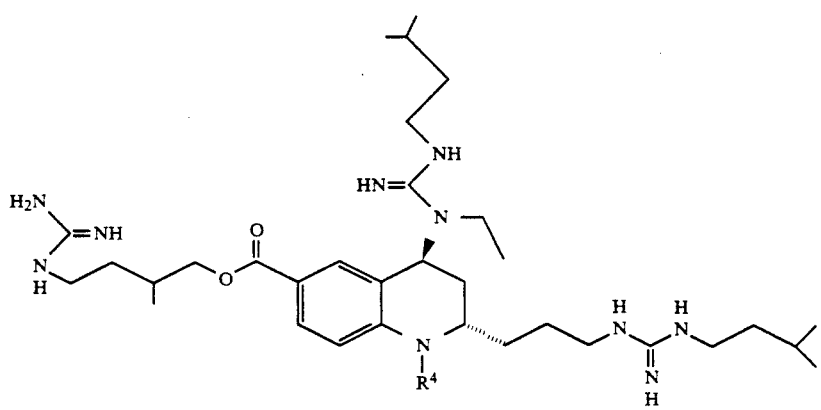

wherein R⁴ is H or CH₃.

4. The compound according to claim 2 and the pharmaceutically acceptable salts of the formula:

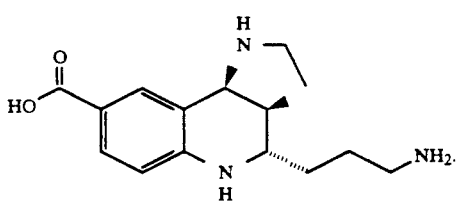

5. A method of inhibiting a bradykinin receptor in a mammal in need of treatment thereof comprising administering a pharmaceutically effective amount of the compound according to claim 1, except that the compound of the formula:

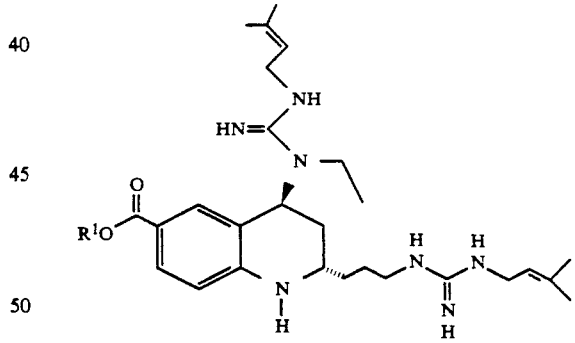

wherein $R^1$ is H or CH₃ is not used as a bradykinin receptor antagonist.

6. A method of inhibiting an $\alpha_1$-adrenergic receptor in a mammal in need of treatment thereof comprising administering a pharmaceutically effective amount of the compound according to claim 1.

7. A method of inhibiting a muscarinic receptor in a mammal in need of treatment thereof comprising administering a pharmaceutically effective amount of the compound according to claim 1.

8. A method of inhibiting an $H_1$-histamine receptor in a mammal in need of treatment thereof comprising administering a pharmaceutically effective amount of the compound according to claim 1.

9. A method of treating pain and inflammation in a mammal in need of treatment thereof comprising administering a pharmaceutically effective amount of the compound according to claim 1.

10. A method of treating allergy symptoms in a mammal in need of treatment thereof comprising administering a pharmaceutically effective amount of the compound according to claim 1.

11. A pharmaceutical composition comprising the compound according to claim 1 and a pharmaceutically acceptable carrier.

12. A method of inhibiting a bradykinin receptor in a mammal in need of treatment thereof comprising administering a pharmaceutically effective amount of the pharmaceutical composition according to claim 11.

13. A method of inhibiting an $\alpha_1$-adrenergic receptor in a mammal in need of treatment thereof comprising administering a pharmaceutically effective amount of the pharmaceutical composition according to claim 11.

14. A method of inhibiting a muscarinic receptor in a mammal in need of treatment thereof comprising administering a pharmaceutically effective amount of the pharmaceutical composition according to claim 11.

15. A method of inhibiting an $H_1$-histamine receptor in a mammal in need of treatment thereof comprising administering a pharmaceutically effective amount of the pharmaceutical composition according to claim 11.

16. A method of treating pain and inflammation in a mammal in need of treatment thereof comprising administering a pharmaceutically effective amount of the pharmaceutical composition according to claim 11.

17. A method of treating allergy symptoms in a mammal in need of treatment thereof comprising administering a pharmaceutically effective amount of the pharmaceutical composition according to claim 11.

* * * * *